United States Patent [19]
Wachspress

[11] 3,954,101
[45] May 4, 1976

[54] AUDIOTACTILE COMMUNICATION SYSTEM

[76] Inventor: How F. Wachspress, 1940 Washington St., San Francisco, Calif. 94109

[22] Filed: Apr. 7, 1975

[21] Appl. No.: 565,466

Related U.S. Application Data

[63] Continuation-in-part of Ser. No. 337,719, March 2, 1973, Pat. No. 3,875,932.

[52] U.S. Cl. .......................... 128/24 R; 128/24 A; 179/107 R
[51] Int. Cl.² ......................................... A61H 1/00
[58] Field of Search ............... 128/1 R, 24 R, 24 A, 128/32, 38–40, 41; 3/1; 179/107 BC, 107 R

[56] References Cited
UNITED STATES PATENTS

| 592,844 | 11/1897 | Waite | 128/24 R |
|---|---|---|---|
| 1,077,096 | 10/1913 | Rosenberg | 128/41 |
| 2,652,048 | 9/1953 | Joers | 128/39 |
| 3,259,205 | 7/1966 | Dubow | 179/107 BC |

*Primary Examiner*—Lawrence W. Trapp
*Attorney, Agent, or Firm*—Gregg, Hendricson, Caplan & Becker

[57] ABSTRACT

A combined stimulator and sensor unit for audiotactile communication may be employed in an array in simultaneous or alternate transmission modes in a system between life forms or receive input and output information.

15 Claims, 2 Drawing Figures

AUDIOTACTILE COMMUNICATION SYSTEM

The present invention is a continuation-in-part of copending U.S. patent application Serial No. 337,719 entitled "Audiotactile Stimulation and Communications System" filed in the U.S. Patent Office on Mar. 2, 1973 and now U.S. Pat. No. 3,875,932

BACKGROUND OF INVENTION

It is known that intelligence can be coupled into life forms such as the human body through the skin and various different types of devices and systems to this end have been investigated. In general the investigations have been directed to the application of very limited intelligence; however, there is disclosed in my above-noted copending patent application a major improvement in audiotactile communication wherein sound waves are coupled into the body through the skin for conveying a wide variety of stimulation and intelligence to the body. Reference is made to the disclosure of such patent application for incorporation herein.

The present invention provides improvements in the audiotactile stimulation and communication system of my copending patent application.

SUMMARY OF INVENTION

One of the substantial applications of an efficient audiotactile communication system is the coupling of music into the human body through the skin and to this end there may be employed various types of recordings from which the sound material is obtained. It has also been recognized that body actions and reactions may be sensed and coupled into the same or other bodies. The present invention is particularly adapted to the generation of sound waves from the body and application of such waves to a body by the provision of a two-way communication system wherein input and output elements are combined or at least disposed in such intimate arrangement as to provide the capability of receiving the results of audiotactile stimulation and transmitting same back to the same life form or another life form.

The present invention provides an audiotactile stimulator and sensor in a single unit with stimulator and sensor being interchangeable. A plurality of these stimulator-sensor units are joined together in a matrix array or the like to provide an area audiotactile device which may be employed to transmit or receive body signals or externally generated signals.

DESCRIPTION OF FIGURES

The present invention is illustrated as to a single preferred embodiment thereof in the accompany drawings wherein.

DESCRIPTION OF PREFERRED EMBODIMENT

Figure 1:
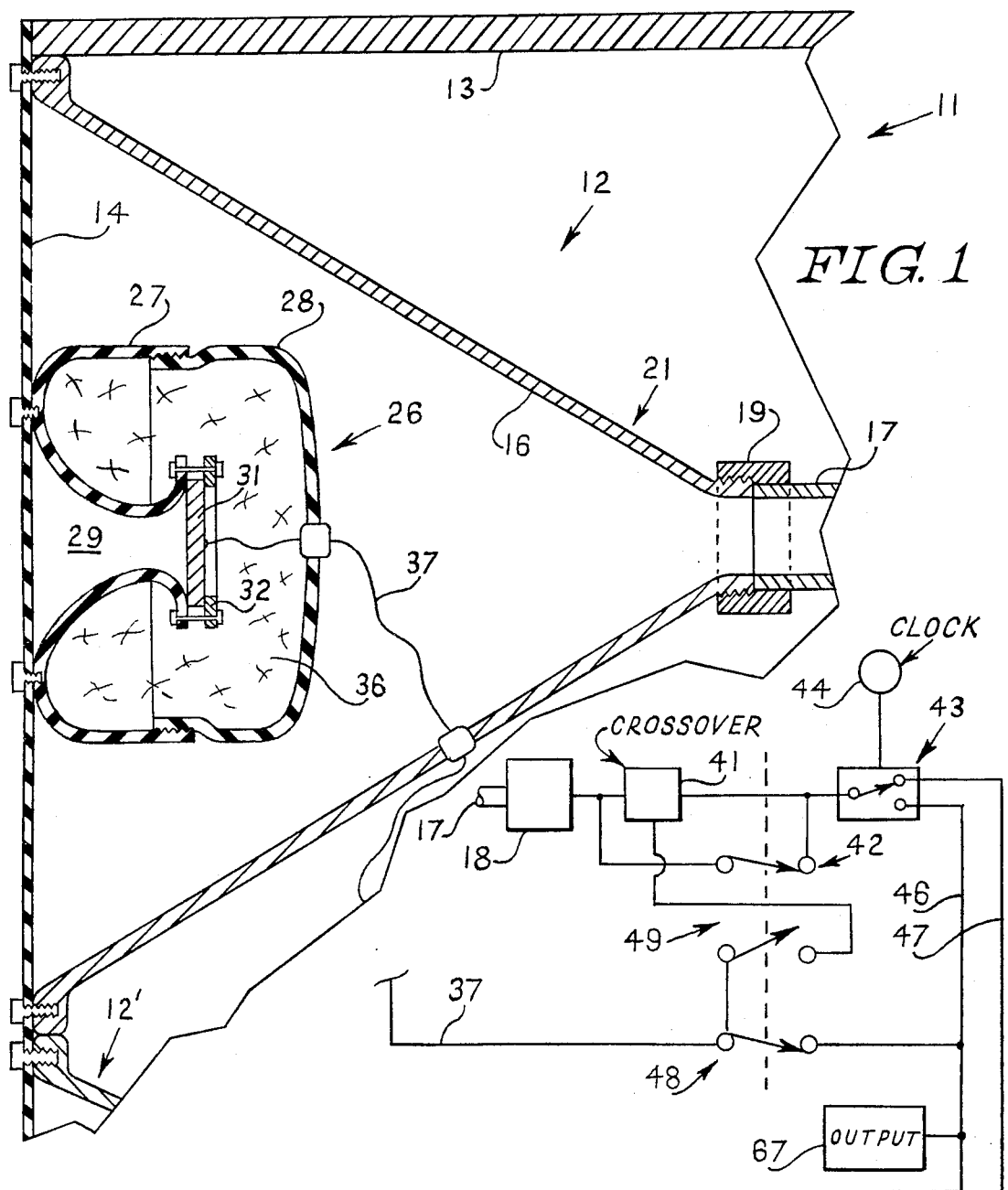
FIG. 1 is a partial sectional view of an audiotactile array in accordance with the present invention.

Referring to the drawings there will be seen to be illustrated in FIG. 1 a part of an array 11 comprising a plurality of units such as the unit illustrated at 12 and the unit partially illustrated at 12'. The array may include a frame 13 in which the units 12, 12', etc. are mounted and across an open face of the frame there is attached a resilient membrane 14 which may, for example, be formed of thin rubber sheet. The unit 12 includes a horn 16 that may be mounted in the frame by attachment at the open end thereof to the membrane 14 by any suitable means compatible with membrane and horn. A waveguide 17 extends from the small end of the horn to a transducer 18 and a coupler 19 is provided to join waveguide and horn. The transducer 18 may, for example, be comprised as one of the transducers described and illustrated in my above-noted copending patent application and is thus not further described herein. As a matter of convenience the horn 16, waveguide 17 and transducer 18 are hereinafter termed a stimulator 21 or output device, although it is possible, as described below, for this portion of the unit 12 to be employed as the input or sensor.

Within the horn 16 there is disposed a unit hereinafter denominated as a sensor 26. The sensor 26 may have somewhat of a spherical configuration and is formed of two portions 27 and 28 which may be joined together as by screw threads, as illustrated. The front portion 27 of the sensor is curved inwardly, as illustrated, to form what may be termed a horn 29 and the inner ends of this inturned portion are flared outwardly within the sensor to provide a support for a piezoelectric crystal or the like 31. The crystal 31 may be mounted within the sensor as by means of a frame 32 with bolts extending through the frame and through the outwardly flared portion of the sensor at the horn 29 about the crystal. The sensor 26 preferably has the shell thereof formed of rubber or the like, as illustrated, and it will be seen that with the illustrated mounting the crystal may be considered to be mounted by vibration isolation means and the sensor shell is considered to be substantially soundproof. This soundproof feature may be aided by the provision of soundproofing material 36 within the sensor shell. It will thus be seen that the sensor 26 comprises a transducer having the basic features of transducer 18 such as illustrated and described in my above-identified copending patent application.

The sensor 26 is mounted on the diaphragm 14 within the horn 16 and in spaced relation to the walls of the horn as by means attaching the sensor to the membrane. One or more electrically conducting wires 37 extend from the piezoelectric crystal through the shell of the sensor and through a wall of the horn 16 for connection into the channel of a system of the present invention. It will be appreciated that the crystal 31 may take a variety of forms and whatever the form, the crystal serves the purpose of producing electric signals upon the application of sound waves thereto and vice versa.

The unit 12 or an array 11 of such unit is adapted to be intimately contacted with the skin of a life form at the membrane 14 thereof. It will thus be appreciated that operation of the transducer 18 by the application of electrical signals thereto will produce sound waves which are efficiently coupled into the waveguide 17 and then through the horn 16 into the skin of the life form through the membrane 14. If, for example, the input signals to the transducer were derived from a musical score, there would then be induced in the skin of the life form or person engaged by the diaphragm 14 audiotactile signals which would be received as the musical score. This method of communication entirely bypasses the ear and yet is accepted by the life form or body as sound. Alternatively, if the input to the transducer 18 was bioelectric signals generated by the same or another life form, these signals would also generate sound waves which would be coupled into the life form or body engaging the diaphragm 14. In the foregoing example it was assumed that the transducer 18 comprised a portion of the input of the unit 12; however, it is possible to alternatively operate the unit 12 to provide input signals through to the lead 17 so as to energize the crystal 31 and thus constitute the "sensor" 26 as a stimulator which applies input signals through the diaphragm 14 to the skin of a body, for example. This is further described below in connection with FIG. 2.

Figure 2:
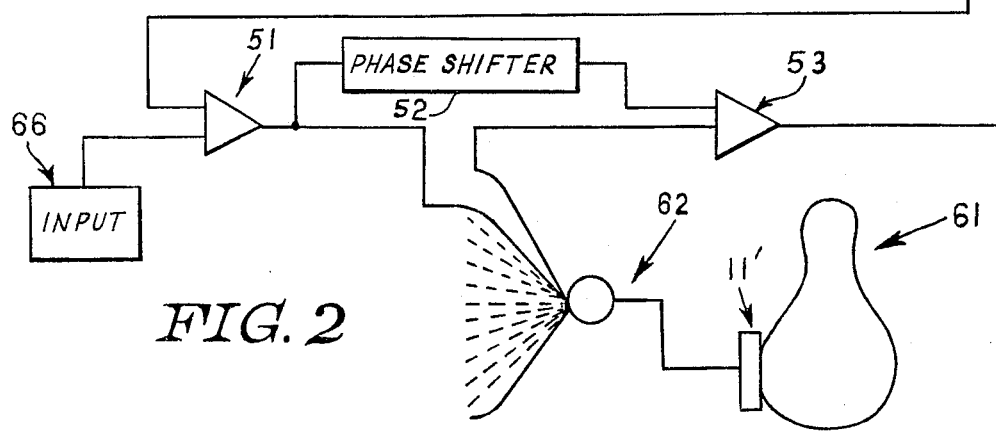
FIG. 2 is a block diagram of an audiotactile system in accordance with the present invention.

Considering now a system in accordance with the present invention, reference is made to FIG. 2 illustrating the waveguide 17 and transducer 18 and also the electrical connection 37. The transducer 18 is shown to be connected to a crossover 41 which is bypassed by a normally closed switch 42. An output of the crossover 41 which is bypassed by the switch 42 is connected to the input of an electronic switch 43 which may be controllably operated by a clock 44 at a controllable clock rate to switch between a pair of lines 46 and 47. The electronic switch 43 is normally in the position illustrated connecting the crossover output to the line 47. The electrical conductor 37 is connected through a normally closed switch 48 to the line 46 and is also connected through a normally open switch 49 to a second output of the crossover 41. The line 37 is connected through the switch 48 to the input of an amplifier 51 which, in turn, is connected through a phase shifter 52 and second amplifier 53 to the line 47. A second array 11' is adapted to be placed in intimate contact with the skin of a second life form or body 61 and the output of the amplifier 51 is connected through one conductor of a cable 62 to one unit 12 of the life form 61.

The second array 11' is comprised as units such as unit 12 of FIG. 1, including the transducer associated with the horn of each unit, and thus for each unit there is an input and output line for the array 11'. The output line which may, for example, correspond to the line 37 of FIG. 1, extends from the array 11' through the cable 62 to an input of the amplifier 53 which, in turn, is connected to the line 47 of the electronic switch 43. In addition to the above-described elements of the system of FIG. 2, there may also be provided an input unit 66 connected to an input of the amplifier 51 for applying externally generated electrical signals to the system. Additionally there may be provided an output unit 67 connected to the line 46 of the system to receive signals generated in the system. The input unit 66 may comprise any of a wide variety of elements such as, for example, tape recorders or the like, upon which there has been recorded signals useful in the system and the output unit 67 may also comprise a wide variety of different elements such as, for example, a transmission medium for coupling signals from the system into other life forms or possibly some type of recording medium for preserving signals generated in the system.

Considering now operation of the system of FIG. 2, it is noted that the switches 42, 48 and 49 are ganged together with the system as illustrated providing switches 42 and 48 in normally closed position and switch 49 in normally open position. Actuation of the gang switch would then place switches 42 and 48 in the open position and switch 49 in the closed position. Assuming initially that the stimulator 21 of the unit 12 is to be employed as an input device to a life form and the element 26 to be employed as an output device that will be produced on the line 37 output signals received from the life form in contact with the diaphragm 14.

Following the circuitry of the system of FIG. 2, it will be seen that these signals are passed through the normally closed switch 48, either to the output 67 for possible recording or other use and also through the amplifier 51 to the phase shifter 52. The purpose of this phase shifter is further described below. The output of the phase shifter is applied through the amplifier 53, the normally closed contacts of electronic switch 43 and the normally closed contacts of switch 42, as an input signal to the transducer 18. Additionally the signal on line 37 appearing at the output of amplifier 51 is applied to a unit 12 of the array 11' engaging the life form 61. Thus, the life form reaction at the diaphragm of unit 12 is applied to a similar diaphragm engaging the life form 61. Likewise an audiotactile output at a unit of the array 11' engaging the life form 61 is applied as an input to the amplifier 51 and thence through the above-described connections as an input to the transducer 18. The life form engaged by the membrane 14 of FIG. 1 receives signals generated by the life form 61 and vice versa while, at the same time, the life form engaging the membrane 14 receives signals generated by the same life form. Considering now the purpose of the phase shifter in this system, it is noted that the normal reaction of the skin of a human being, for example, pressed against an immovable object, is to receive an equal and opposite force from the object. In order to combine the stimulator and sensor of the present invention in a single unit, the present invention may employ the phase shifter 52 to provide a 180° phase shift in order that a pressure exerted on the skin by either the sensor or stimulator of the unit 12 will not be opposed by a signal on the other one of these elements. It is possible to employ the phase shifter to insert some phase shift other than 180° so that varying degrees of resistance to the application of force to the skin may be experienced. In the simplest example it may be considered that the phase shifter 52 is a phase inverter; however, in actual practice the phase shift may or may not be 180°.

The present invention is capable of operation in a variety of different modes and the one described above is a simultaneous mode. An alternate mode of operation is possible by operation of the electronic switch 43 at some rate determined by the clock 44 which, as noted above, is manually adjustable as to the rate thereof. With the switch 43 operated at some clock rate, the signals applied to the transducer 18 will be alternately generated from the sensor 26 of the unit 12 and from a sensor of the array 11'.

In addition to the foregoing modes of operation of the present invention it is possible to operate the switches 42, 48 and 49 so as to insert the crossover 41 in the circuit of the system. It will be appreciated that a crossover is a conventional electronic circuit component generally comprised as a high-frequency filter and low-frequency filter so that high-frequency components of an input signal appear at one output and low-frequency components thereof appear at another output. With the crossover 41 inserted in the circuit by operation of the ganged switches, the unit 12 may be employed to apply low-frequency signals to the horn 16 and high-frequency signals through the sensor 26, or even vice versa, although this latter alternative is not too practical.

The system of FIG. 2 has been described with reference to the utilization of an array 11 and, in this connection, it is noted that the circuitry of FIG. 2 relates only to one channel of such an array. Each channel of the array would be operated upon in the same manner as that illustrated in FIG. 2 and described above and this is generally indicated by the multiplicity of inputs and outputs at cable 62 of FIG. 2. It is, of course, also possible to employ the present invention with only a single stimulator and sensor and it is not intended by the illustration and foregoing description to preclude such operation. With a single stimulator 21 and sensor 26 it is possible to employ such a unit 21 as an input/output device with the stimulator and sensor being interchangeable with regard thereto and also to employ the device as a separate low-frequency and high-frequency input or output. It is again noted that the sensor 26 is, in fact, a smaller edition of a transducer such as described in my above-noted copending patent application in that it includes a substantially soundproof container having the transducer therein mounted by vibration isolating means for substantially coupling sound through the horn 27 thereof rather than radiating sound. Additionally a single unit 12 may be employed in the simultaneous or alternating mode, as described above in connection with the system of FIG. 2.

The present invention has been described above with respect to a single preferred embodiment thereof; however, it will be apparent to those skilled in the art that numerous modifications and variations are possible within the scope of the present invention and thus it is not intended to limit the invention to the precise terms of description nor details of illustration.

What is claimed is:

1. An audiotactile communication system comprising an audiotactile sensor including a transducer producing electrical signals responsive to applied sound waves and means for coupling said transducer to the skin of a life form for producing electrical signals representing movement of said skin against the sensor.

an audiotactile stimulator including an audiotactile transducer producing sound waves from applied electrical signals and having a sound waveguide extending therefrom with means for coupling same to the skin of a life form, and means including an amplifier connecting said sensor and stimulator for audiotactile communication between life forms.

2. The system of claim 1 further defined by said stimulator includinig a horn extending outwardly from the end of said waveguide with a flexible diaphragm across the large end thereof adapted to engage the skin of a life form, and a second audiotactile sensor mounted within said horn in position to receive sound waves generated by said diaphragm for producing electrical signals responsive thereto.

3. An audiotactile input-output unit comprising a first audiotactile transducer coupled to a horn extending outwardly therefrom with a flexible diaphragm across the large end thereof for contacting the skin of a life form and having electrical connections extending from said transducer, and a second audiotactile transducer disposed within said horn out of closing relationship therewith and communicating with said diaphragm and having electrical connections thereto.

4. An audiotactile array comprising a plurality of audiotactile units as defined in claim 3 with a single flexible diaphragm common to each unit being mounted on a frame whereby a plurality of input signals may be coupled into a life form over an area of skin thereof and a plurality of electrical signals may be generated thereby.

5. An audiotactile system for audiotactile communication between life forms comprising a pair of audiotactile arrays as defined in claim 4 adapted to contact separate life forms and interconnected by means including an amplifier and connecting the sensors of a first array to the stimulators of a second array and the sensors of the second array to the stimulators of the first array.

6. The system of claim 5 further defined by said means interconnecting said arrays also connecting the sensors of the first array to the corresponding stimulators of the first array through phase-shifting means.

7. The audiotactile unit of claim 1 further defined by said first transducer comprising a stimulator adapted to receive electrical signals for coupling sound waves into the skin of a life form through said diaphragm and said second transducer having a horn inlet mounted on said diaphragm and comprising a sensor producing electrical signals from diaphragm vibrations.

8. An audiotactile communication system comprising a first audiotactile stimulator and sensor unit having a flexible diaphragm adapted to contact the skin of a life form with electrical connections to stimulator and sensor, a second audiotactile stimulator and sensor unit having a flexible diaphragm adapted to contact the skin of a life form with electrical connections to stimulator and sensor, and electrical circuitry interconnecting said first and second stimulator and sensor units for application of audiotactile signals between life forms.

9. The communication system of claim 8 further defined by said electrical circuitry including connections including a phase shifter interconnecting the sensor and stimulator of each unit.

10. The communication system of claim 9 further defined by said phase shifter comprising a phase inverter.

11. The communication system of claim 9 further defined by electronic switching means operated at a clock rate alternately applying to each stimulator electrical signals from the sensor of the same unit and the sensor of the other unit.

12. The communication system of claim 8 further defined by input means connected to said electrical circuitry for applying externally generated signals thereto and a crossover unit having high-pass and low-pass filters with an input thereof coupled to said input means and separate high-frequency and low-frequency outputs connected to the sensor and stimulator of each of said units whereby the sensor operates as a high-frequency audiotactile stimulator and the stimulator operates as a low-frequency audiotactile stimulator.

13. An audiotactile communication system comprising an audiotactile transducer for generating electrical signals from incident sound waves, sound waveguide means connected to said transducer and adapted for intimate coupling to a life form for directing sound waves generated by the life form to said transducer, and output means electrically connected to said transducer for utilization of said transducer signals.

14. The system of claim 13 further defined by said transducer being disposed in a substantially sound proof container coupled to said waveguide.

15. The communication system of claim 13 further defined by said transducer being disposed in a housing integral with said sound waveguide.

* * * * *